(12) United States Patent
Peltier

(10) Patent No.: US 8,991,609 B2
(45) Date of Patent: Mar. 31, 2015

(54) TRAY FOR CARRYING A PLURALITY OF FLASKS

(75) Inventor: Eric Peltier, Clamart (FR)

(73) Assignee: NOVACYT, Velizy Villacoublay (FR)

( * ) Notice: Subject to any disclaimer, the term of this patent is extended or adjusted under 35 U.S.C. 154(b) by 165 days.

(21) Appl. No.: 12/527,254

(22) PCT Filed: Feb. 13, 2008

(86) PCT No.: PCT/FR2008/050232
§ 371 (c)(1),
(2), (4) Date: Aug. 14, 2009

(87) PCT Pub. No.: WO2008/104710
PCT Pub. Date: Sep. 4, 2008

(65) Prior Publication Data
US 2010/0089925 A1    Apr. 15, 2010

(30) Foreign Application Priority Data

Feb. 16, 2007 (FR) ...................... 07 53311

(51) Int. Cl.
| | |
|---|---|
| B65D 21/02 | (2006.01) |
| B01L 3/00 | (2006.01) |
| B01L 9/06 | (2006.01) |
| G01N 35/02 | (2006.01) |

(52) U.S. Cl.
CPC ................ B01L 9/06 (2013.01); B01L 3/5082 (2013.01); G01N 35/026 (2013.01)
USPC ..... 206/564; 206/565; 220/23.88; 220/23.86; 220/628; 220/636

(58) Field of Classification Search
CPC ........................ B65D 21/0233; B65D 21/0209
USPC ............... 220/628, 23.88, 23.4, 23.89, 23.86, 220/23.83, 625, 630, 636; 206/564, 565, 206/483, 477, 145, 153; 211/71.01; 248/311.2, 346.01, 346.03, 346.06
See application file for complete search history.

(56) References Cited

U.S. PATENT DOCUMENTS 3,193,107 A * 7/1965 Pilat ................................ 211/74
3,993,452 A   11/1976 Moulding
(Continued)

FOREIGN PATENT DOCUMENTS

| JP | 9-15246 | 1/1997 |
|---|---|---|
| WO | 02/082095 | 10/2002 |
| WO | 2006/058989 | 6/2006 |

OTHER PUBLICATIONS

International Search Report dated Sep. 5, 2008, from corresponding PCT application.

*Primary Examiner* — Stephen Castellano
(74) *Attorney, Agent, or Firm* — Young & Thompson

(57) ABSTRACT

A tray for carrying at least one bottle that has to be positioned and held precisely on the tray, includes a support on which the bottle is intended to be placed, at least two rails running substantially parallel to one another along the support, the rails including at least one shoulder extending above the support toward the other rail so that a lower edge of the bottle can fit between and be immobilized in the rails in a longitudinal or transverse direction and in an upwards direction, each rail having at least one imprint, the imprints being positioned facing one another, each imprint being designed to accommodate an immobilizing element provided on the bottle so that the bottle can be immobilized in the rails in a longitudinal or transverse direction. A bottle used with a tray such as this is also described.

10 Claims, 4 Drawing Sheets

(56) References Cited

U.S. PATENT DOCUMENTS

Figure 1:
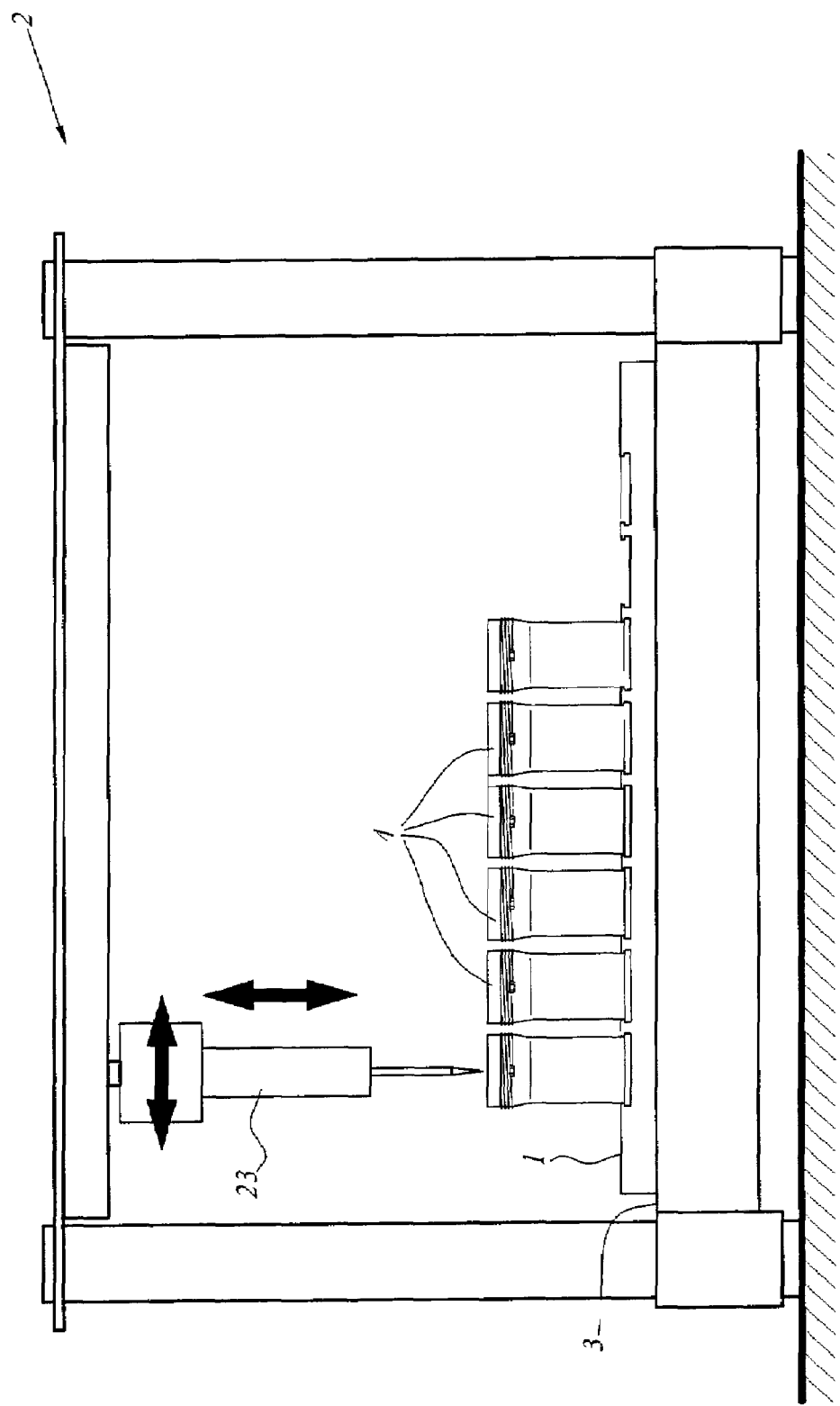

| | | | |
|---|---|---|---|
| 5,112,574 A | 5/1992 | Horton | |
| 5,651,941 A | 7/1997 | Stark et al. | |
| 5,702,041 A * | 12/1997 | Sun et al. | 224/539 |
| 5,878,986 A * | 3/1999 | Sun et al. | 248/311.2 |
| 5,941,366 A | 8/1999 | Quinlan et al. | |
| 2008/0070295 A1 | 3/2008 | Peltier | |

* cited by examiner

TRAY FOR CARRYING A PLURALITY OF FLASKS

BACKGROUND OF THE INVENTION

1. Field of the Invention

The invention relates to a tray for carrying at least one flask, especially in the field of laboratory medicine, and to a flask adapted to cooperate with said tray.

2. Description of the Related Art

It is known to arrange a plurality of flasks on a tray and to insert the tray into a machine for carrying out filling or sampling of the contents of the flasks. The flasks are held on the tray, which moves beneath the machine or above which a machine comprising filling or sampling means moves.

Such machines are used more particularly in the biological field and more particularly in the field of laboratory medicine. Precise positioning of the flasks must be ensured so that the filling or sampling means of the machine are correctly located opposite a flask during those operations. In addition, the flasks must be held firmly on the tray in order to prevent them from moving and changing position or from falling over.

Such positioning and holding are more particularly important for some types of flask. In the field of preparation of laboratory medicine, flasks are known which are closed by a cap which has a pierceable and self-sealing portion for the passage of a suction pipette provided on the machine. Such a flask is described, for example, in document WO-2006/058989. In the case of such a flask, it is necessary to prevent the pipette from moving the flask on the tray as it passes through the pierceable portion and, more particularly, to prevent the pipette from lifting the flask as it is withdrawn.

On some flasks, means of identifying the flask which can be read remotely, for example by means of a camera, a CCD sensor, etc., are also provided. The identification means, such as a bar code, of all the flasks must then be oriented in the same direction in order to permit reading. Precise positioning of the flasks on the tray is therefore of the utmost importance.

It is estimated that the flasks must be positioned to within one tenth of a millimeter in the longitudinal and transverse directions of the tray in order for the machine to operate correctly.

SUMMARY OF THE INVENTION

The invention aims to achieve that object by proposing a tray for receiving flasks and a flask which ensure that the flasks are positioned precisely in the longitudinal and transverse directions of the tray and that the flasks are held in those directions and in an elevation direction.

To that end and according to a first aspect, the invention relates to a tray for receiving at least one flask which is to be positioned and held precisely on said tray, said tray having a support on which the flask is to be placed, at least two rails which extend substantially parallel to one another on the support, said rails having at least one shoulder which extends above the support towards the other rail so that a lower edge of the flask is able to fit and be immobilised between said rails in a longitudinal or transverse direction and in an elevation direction, each rail having at least one indentation, said indentations being arranged facing one another, each indentation being designed to receive an immobilisation means provided on the flask so that the flask can be immobilised between the rails in a longitudinal or transverse direction.

According to other features of the tray:
- it has a plurality of rails associated with one another so as to form a comb, said rails forming a plurality of rows suitable for receiving a plurality of flasks,
- it has two end rails each having a shoulder extending towards the other end rail, and a plurality of central rails each having two shoulders, each of which extends towards one of the end rails,
- each rail has a plurality of indentations distributed along said rail so that a plurality of flasks can be received in a row formed by two rails.

According to a second aspect, the invention relates to a flask for use with a receiving tray as described hereinbefore, said flask having a body from which there extends a lower edge forming a means for immobilising the flask between two rails of the tray in a longitudinal or transverse direction and in an elevation direction, said flask further having immobilisation means which are arranged on either side of the body and project therefrom, said means being intended to engage in the indentations of the rails of the tray so as to immobilise the flask in a longitudinal or transverse direction.

According to other features of the flask:
- the immobilisation means comprise a projection arranged on a tab provided in the lower portion of the body, said tab being substantially resilient so as to obtain a spring effect which allows the projection to engage in an indentation when they are facing one another,
- the body has an area around the tab from which material has been removed,
- the flask has a cap, the body having in its upper portion means for receiving the cap, said receiving means comprising at least one element for positioning the cap so as to orient it in a predefined manner,
- the receiving means are formed by a thread on the upper portion of the body, the positioning element being formed by a stop which projects from the thread, the cap having screwing means complementary to the thread and a counter-stop on which the stop abuts when the cap is screwed fully onto the body,
- the cap bears a visual marking, said marking being oriented in a precise and invariable direction when the cap is fixed on the body.

BRIEF DESCRIPTION OF THE DRAWING FIGURES

Figure 2:
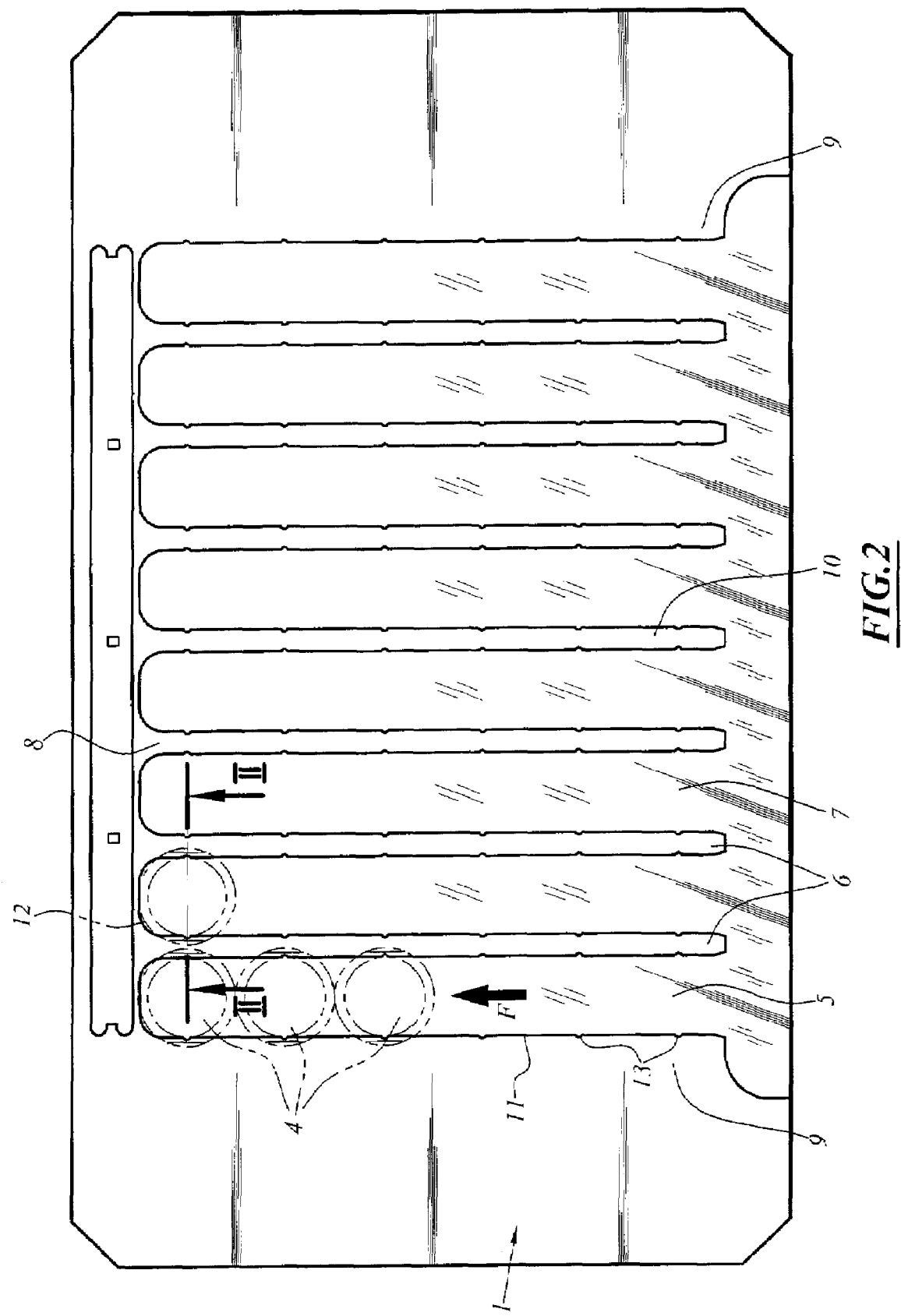
Figure 3:
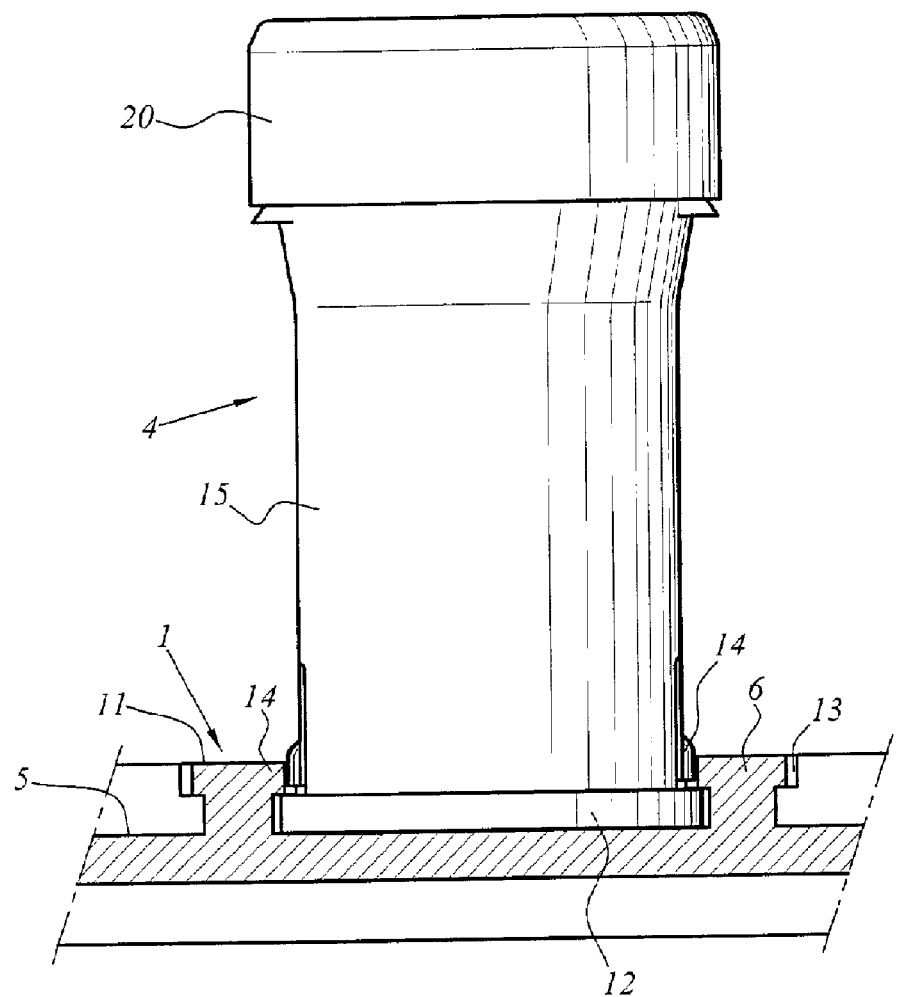
Figure 4:
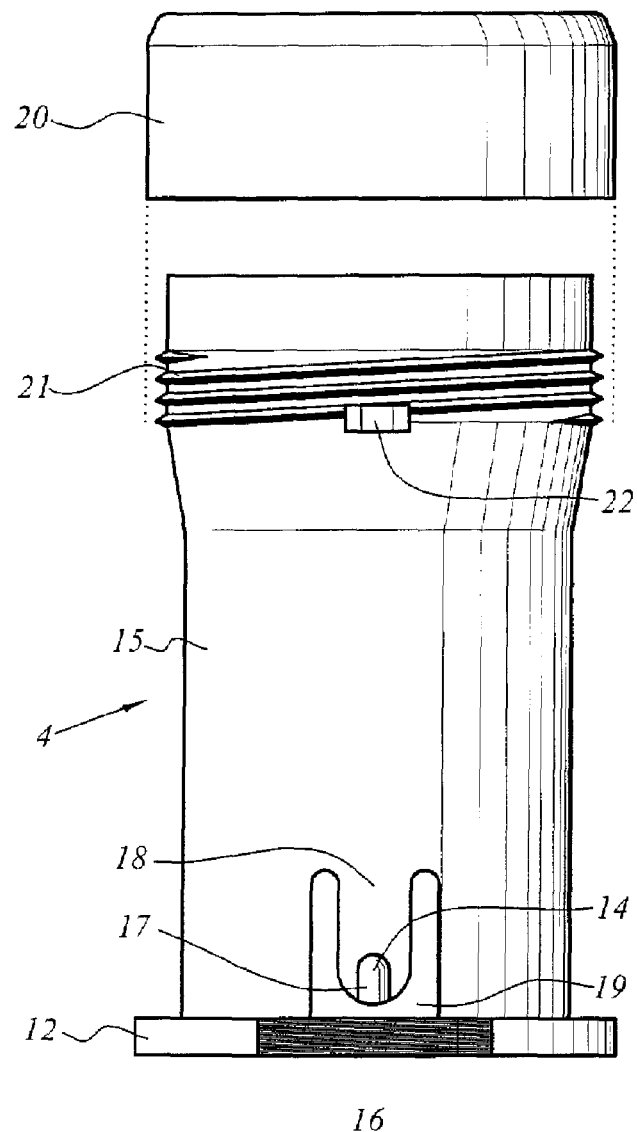

Other aspects and advantages of the invention will become apparent from the following description, which is given by way of example and with reference to the accompanying drawings, in which:

FIG. 1 is a perspective view of a machine used with a receiving tray carrying flasks according to the invention, FIG. 2 is a diagrammatic top view of a receiving tray according to the invention, flasks being shown by dotted lines, FIG. 3 is a diagrammatic cutaway view according to the axis II-II of FIG. 1, FIG. 4 is a diagrammatic side view of a flask according to the invention, the cap having been removed from said flask.

DETAILED DESCRIPTION OF THE INVENTION

In the description, the term "longitudinal" is defined in a direction parallel to the largest side of the receiving tray, and the term "transverse" is defined in a direction parallel to the smallest side of the tray. The term "elevation" is defined in a direction perpendicular to the plane formed by the longitudinal and transverse directions.

The receiving tray 1 is to be used with a machine 2 as shown in FIG. 1. The machine 2 has a support 3 on which there is arranged the tray 1 carrying flasks 4 and above which there extend filling or sampling means 23. The means 23 are movable so as to pass above each flask 4 in order to carry out sampling or filling as shown by the arrows of FIG. 1. The machine 2 is conventional for this type of application and is not described in further detail.

The tray 1 has a support 5 on which the flasks 4 are arranged between rails 6. The rails 6 extend on the support 5 parallel to one another so as to form rows into which the flasks can be introduced. According to the embodiment shown in the figures, the rails 6 extend in a transverse direction. According to a variant, the rails 6 can extend in a longitudinal direction. The rails 6 form an opening 7 at one end so as to permit the insertion of flasks 4 between them, as shown by arrow F in FIG. 2. The rails are connected together at their other end so that the totality of the rails 6 forms a comb 8, as shown in FIG. 2.

The comb 8 has two end rails 9 on either side of the support 5 and a plurality of central rails 10 arranged between the end rails 9. The end rails 9 are each provided with a shoulder 11 which extends above the support towards the other rail. The central rails 10 are each provided with two shoulders 11, each of which extends above the support 5 towards one of the end rails, as shown in FIG. 3. A lower edge 12 of the flask 4 can thus be fitted between the rails and beneath the shoulders 11 so as to be immobilised in the elevation direction and in the longitudinal or transverse direction.

Each rail 6 has a plurality of indentations 13 spaced evenly along the rail. The indentations 13 of two adjacent rails 6 are arranged facing one another. The indentations 13 are provided to cooperate with immobilisation means 14 for the flasks 4, as will be described hereinbelow.

A flask 4 which is to be arranged on the tray 1 described above will now be described. The flask 4 can have the same features as those described in document WO-2006/058989.

The flask 4 has a body 15, for example a substantially cylindrical body. A lower edge 12 extends from the body 15, allowing the flask 4 to be immobilised between the rails 6 as mentioned hereinbefore. The edge 12 surrounds the body 15 and is substantially cylindrical. Reserves 16 are provided in the edge 12, however, so that the flask has substantially flat edge portions. The flask 4 can accordingly be introduced between the rails 6 in only one direction, the distance separating said rails in the region of the support 5 corresponding substantially to the distance separating the substantially flat edge portions 12.

At a height corresponding to that of the indentations 13 of the tray 1, the body 15 has immobilisation means 14 arranged in the region of the substantially flat edge portions 12, as shown in FIG. 4. The flask 4 has two immobilisation means 14 each arranged facing a shoulder 11 of a rail 6 when the flask 4 is arranged on the tray 1. The immobilisation means 14 comprise a projection 17 projecting from a tab 18 provided in the body 15. The projection 17 is suitable for engaging in an indentation 13 of a rail 6 so as to immobilise the flask 4. The tab 18 is substantially resilient so as to obtain a spring effect which allows the projection 17 to engage in an indentation 13 when they are facing one another. That resilience is obtained, for example, by removing material from an area 19 of the body 15 around the tab 18. The distance separating each rail 6 in the region of the shoulders 11 corresponds substantially to the diameter of the body of a flask 4, so that the projection 17 engages inevitably in an indentation 13 when it is located opposite one of the indentations.

The flask 4 has a cap 20, for example provided with a pierceable and self-sealing portion permitting the passage of a pipette. The body 15 has in its upper portion receiving means 21 for the cap 20. The receiving means are formed, for example, by a thread on the upper portion of the body, the cap having screwing means complementary to the thread.

The receiving means 21 comprise at least one element 22 for positioning the cap 20 so that it is oriented in a predefined manner. The positioning element 22 is formed, for example, by a stop which projects from the thread. The cap has a counter-stop (not shown) on which the stop abuts when the cap 20 is screwed fully onto the body 15. According to an embodiment, the positioning element 22 is arranged in the region of the immobilisation means 14, as shown in FIG. 4.

Such an embodiment, in which the caps 20 of all the flasks 4 present on the tray are oriented in the same direction, is particularly advantageous when the cap 20 bears a visual marking (not shown). The marking is then oriented in a precise and invariable direction when the cap 20 is fixed on the body 15, which allows means for remotely reading the marking to be used easily.

Owing to the specific orientation of the flasks, such remote reading means can offer unitary or multiple visualisation of the flasks in order to match them in a unitary or multiple manner with the envisaged analysis system (spread plates, sampling or aliquoting tube, analysis well, etc.), which itself has a fixed position. That is to say, the reading means make it possible to read the marking of a single flask or a plurality of markings at the same time. That fixed positioning, which corresponds, for example, to analysis plates positioned in a decantation press, is made as a continuation of the rails serving to support the flasks, so that a single tray permits correct positioning of the flasks and of the plates for remote reading means offering unitary or multiple visualisation. Accordingly, treatment of the flasks in groups is possible, which permits a greater analysis rate.

The invention claimed is:

1. An assembly, comprising:
   at least one flask and a tray for receiving said flask which is to be positioned and held precisely on said tray;
   said flask having a body from which extends a lower edge;
   said flask having immobilisation elements arranged on either side of the body and projecting from the body;
   said means for immobilisation elements comprising a projection arranged on a tab provided in a lower portion of the body, said tab being substantially resilient so as to obtain a spring effect;
   said tray having a support on which the flask is to be placed;
   at least two substantially parallel rails on the support, the rails forming an opening at one end of the rails so as to permit insertion of flasks between the rails, said rails having at least one shoulder which extends above the support towards the other rail so that a lower edge of the flask is able to fit and be immobilised between said rails in a longitudinal or transverse direction and in an elevation direction, said shoulder extending along the whole length of the rails;
   at least one indentation in each rail, said indentations being arranged facing one another, each indentation being designed to receive the projection provided on the flask, so that the flask can be immobilised.

2. The assembly according to claim 1, wherein the rails form a comb, said rails forming a plurality of rows suitable for receiving said at least one flask.

3. The assembly according to claim 2, wherein the tray has two end rails each having the shoulder extending towards the other end rail, and a plurality of central rails each having two shoulders, each of which extends towards one of the two end rails.

4. The assembly according to claim 3, wherein each rail has a plurality of the indentations distributed along said rail so that a plurality of the flasks can be received.

5. The assembly according to claim 2, wherein each rail has a plurality of the indentations distributed along said rail so that a plurality of the flasks can be received.

6. The assembly according to claim 1, wherein each rail has a plurality of the indentations distributed along said rail so that a plurality of the flasks can be received.

7. An assembly, comprising:
   at least one flask and a tray for receiving said at least one flask, which is to be positioned and held precisely on said tray;
   said tray having a support on which the at least one flask is to be placed;
   said support having at least two rails which extend substantially parallel to one another on the support;
   an opening formed at one end of the at least two rails, the opening being configured to permits insertion of the at least one flask between the at least two rails;
   at least one shoulder of said at least two rails, the at least one shoulder extending above the support towards the other rail so that a lower edge of the at least one flask is able to fit and be immobilised between said rails in a longitudinal or transverse direction and in an elevation direction, said at least one shoulder extending along a whole length of the rails; and
   at least one indentation in each rail said indentations being arranged facing one another, each indentation being designed to receive immobilization elements projecting from a tab provided on the at least one flask so that the at least one flask can be immobilised between the at least two rails.

8. The assembly according to claim 7, wherein the support has a plurality of rails associated with one another so as to form a comb, said plurality of rails forming a plurality of rows suitable for receiving a plurality of flasks.

9. The assembly according to claim 8, wherein the support has two end rails each having the shoulder extending towards the other end rail, and a plurality of central rails each having two shoulders, each of which extends towards one of the end rails.

10. The assembly according to claim 7, wherein each rail has a plurality of the indentations distributed along said rail so that a plurality of flasks can be received in a row formed by the at least two rails.

* * * * *